(12) United States Patent
Iltis et al.

(10) Patent No.: US 10,509,134 B2
(45) Date of Patent: Dec. 17, 2019

(54) COMPTON CAMERA SYSTEM AND METHOD FOR DETECTING GAMMA RADIATION

(71) Applicant: Alain Iltis, Troyes (FR)

(72) Inventors: Alain Iltis, Troyes (FR); Hichem Robert René Snoussi, Breviandes (FR)

(73) Assignee: Alain Iltis, Troyes (FR)

( * ) Notice: Subject to any disclaimer, the term of this patent is extended or adjusted under 35 U.S.C. 154(b) by 0 days.

(21) Appl. No.: 15/574,721

(22) PCT Filed: May 13, 2016

(86) PCT No.: PCT/FR2016/051150
§ 371 (c)(1),
(2) Date: Apr. 20, 2018

(87) PCT Pub. No.: WO2016/185123
PCT Pub. Date: Nov. 24, 2016

(65) Prior Publication Data
US 2018/0217276 A1   Aug. 2, 2018

(30) Foreign Application Priority Data

May 18, 2015 (FR) ...................................... 15 54435

(51) Int. Cl.
*G01T 1/20* (2006.01)
*G01T 1/164* (2006.01)
(Continued)

(52) U.S. Cl.
CPC .............. *G01T 1/2018* (2013.01); *A61B 6/02* (2013.01); *G01T 1/1642* (2013.01); *G01T 1/1647* (2013.01); *G06T 7/10* (2017.01)

(58) Field of Classification Search
CPC ..... G01T 1/164; G01T 1/1642; G01T 1/1647; G01T 1/2985; G01T 1/1644; G01T 1/2018; A61B 6/02; G06T 7/10
(Continued)

(56) References Cited

U.S. PATENT DOCUMENTS

| 2002/0008205 A1 | 1/2002 | Kurfess et al. |
| 2002/0011571 A1* | 1/2002 | Lin ........................ G01T 1/2018 250/366 |
| 2015/0331118 A1 | 11/2015 | Iltis |

FOREIGN PATENT DOCUMENTS

FR          2997766          5/2014

OTHER PUBLICATIONS

International Search Report for corresponding International PCT Application No. PCT/FR2016/051150, dated Aug. 30, 2016, pp. 1-4.

\* cited by examiner

*Primary Examiner* — David P Porta
*Assistant Examiner* — Meenakshi S Sahu
(74) *Attorney, Agent, or Firm* — Hauptman Ham, LLP

(57) ABSTRACT

A Compton camera system and method for detecting gamma radiation, comprising a gamma radiation source, at least one fast scintillator plate P1 of which the rise time to peak light is less than 1 ns, having a thickness greater than or equal to 5 mm, equipped with an array of segmented photodetectors (5) and a dedicated fast-reading microelectronic means. The system is characterised in that it is capable of measuring the spatial and temporal coordinates (X, Y, Z, T) and energy E at at least two successive positions of a gamma photon when said photon undergoes Compton scattering at a first point A before being absorbed at a second point B, by recognising circles of non-scattered photons corresponding to each scin-
(Continued)

tillation interaction. The system has a module for estimating a valid Compton event. The detection system has two scintillator plates P1 and P2.

14 Claims, 3 Drawing Sheets

(51) Int. Cl.
    *G06T 7/10*     (2017.01)
    *A61B 6/02*     (2006.01)

(58) Field of Classification Search
    USPC .................................................. 250/370.09
    See application file for complete search history.

COMPTON CAMERA SYSTEM AND METHOD FOR DETECTING GAMMA RADIATION

TECHNICAL FIELD OF THE INVENTION

The invention relates to gamma ray source imaging. More particularly, the invention relates to a system for detecting gamma rays of Compton camera type for reconstructing an image of the gamma sources, precisely measuring the spatiotemporal coordinates and their energies when said photons undergo Compton deviation. The invention further relates to use of the detection system in the fields particularly of astronomy, nuclear industry and medicine. The invention further relates to the processing of the Compton effect in temporal cameras.

STATE OF THE PRIOR ART

At the present time, gamma ray (>30 KeV) sources imaging is essentially performed for medical diagnosis purposes based on two techniques: PET and SPECT. SPECT is based on scintigraphy and produces images and reconstructions in three dimensions of organs and their metabolism by means of an array of gamma cameras revolving around a patient. SPECT can use several energies of gamma rays, but the lead collimator which knows their arrival direction absorbs over 99%. PET uses a ring of segmented detectors. For PET, radiopharmaceutical positron-emitter compounds are used. These produce a pair of photons of 511 KeV, the emission of which can be located due to their simultaneous detection on the ring of detectors. But the radioelements used for PET have a short life and are therefore costly.

A third technique, the Compton camera, is currently emerging. Just as SPECT does, this technology produces an image irrespective of the energy of the gamma, but contrary to SPECT all photons can contribute to the image. But applications of the Compton camera these days are limited by its cost, the high level of noise and the difficulty in getting precise reconstructions.

When scintillating crystals are used to create an image of gamma radiation sources, the probabilistic nature of the gamma photon/matter interaction is posed. Essentially two effects are seen: first the gamma photon can be absorbed at any depth on its propagation path (Depth of Interaction effect). The second effect consists of all current imaging systems (matrix of pixels or Anger camera) being based on the premise that the place where maximum light emission occurs is the place where the gamma photon has been detected.

Due to Compton deviation, this premise is just on the average of a large number of events. By comparison, in the case of a scanner of PET type if the position of a single event is reconstituted, the error on the position can be several millimeters. The adopted solution is then to reject those events for which the deposited energy is not correct. This leads to rejecting a large number of events.

The aim is to present a method for treating Compton scattering in a novel type of detector, the "time camera" described in French patent applications Nos. 1260596 and 1454417 by the same applicant, and describe the operation of a Compton camera based on this type of "time camera" detector.

Techniques for processing Compton scattering have to date enjoyed limited success, since to function Compton cameras need a precise location of at least two localized events in two separate places, for example on at least two plates (plate 1 & plate 2) and precise measuring of the energy deposited at each place on each plate. For this reason, to date all functional Compton cameras have been made with semi-conductors.

Compton cameras made with semi-conductors have the following problems: First, the stopping ability of semi-conductor crystals is low. Considerable thicknesses greater than 30 mm are therefore needed to absorb >80% of the radiation at 511 KeV. These crystals must be segmented, each pixel being read separately, and this increases the cost of the system.

The second problem consists of the cost of the crystal functionalized at $cm^3$ being high (about 2000$/cm3) which limits cameras in small systems.

Another problem of Compton cameras made in this way is that the time response of semi-conductors is slow, over 10 ns. However, many parasite events are measured during the measuring of a Compton event, meaning that there is substantial noise.

The aim of the invention is therefore to propose a technical solution enabling precise determination of coordinates (X, Y, Z, T, E) of each gamma event in the event where the incident photon has undergone Compton scattering by using the principles of the time camera.

The invention thus proposes a detector of Compton camera type having the following advantages:
  It is a detector of type spectrometer and imager and it therefore measures both the energy of gamma photons and their spatial distribution.
  The detector operates for any energy of the gamma photon, as compared to PET technique. Even if this concept operates even better if the energy is high due to the focalization of the deposit of energy in the direction of propagation of the gamma ray.
  The detector can use all the incident gamma photons due to the absence of a collimator, as compared to SPECT.

The main aim of the invention is therefore to propose a novel technique to
  conserve a good location of each event in a detector of time camera type in the event where the photon has undergone a Compton effect;
  measure the energy of an event in a detector of time camera type in the event where the photon has undergone a Compton effect; and
  produce an improved Compton camera by combining one or more detectors of time camera type.

DESCRIPTION OF THE INVENTION

The invention relates to a system for detecting gamma radiation, of Compton camera type, comprising a source of gamma radiation, at least one rapid scintillator plate P1 whereof the rise time to light peak is less than 1 ns, having a thickness greater than or equal to 5 mm, equipped with an array of segmented photodetectors and dedicated rapid reading micro-electronics; the system is characterized in that it is capable of measuring the spatiotemporal coordinates (X, Y, Z, T) and the energy E in at least two successive positions of a gamma photon when said photon undergoes Compton deviation at a first point A before being absorbed at a second point B, by recognizing circles of unscattered photons corresponding to each scintillation interaction.

According to the invention, the system for detecting gamma radiation, of Compton camera type, is characterized in that it comprises a single scintillator plate P1 having a thickness greater than or equal to the average free path of the gamma ray in the relevant crystal.

Also, the system for detecting gamma radiation, of Compton camera type, comprises two photodetector arrays disposed respectively on an input face and on an output face of said scintillator plate P1.

Advantageously, the input face and the output face of the scintillator plate being coupled to the photodetector array are polished and the coupling between said faces and the photodetector array is made by a media of index n less than 1.5 to arrange a total reflection angle. In this case, a double reading of the same event is realized, which improves reconstruction and reduces noise.

Also, lateral faces and the input face of the scintillator plate P1 not being coupled to a photodetector array are rough and said faces are treated such that the absorption of incident photons or the diffuse reflection of photons, there is a maximum. Absorbent processing is applied when the aim is to measure the energy of interactions by the temporal method.

If there is no double reading and if the energy is measured according to the temporal method, the input face of the plate P1 not coupled to a photodetector array is painted black to limit the reflection on said face.

If the aim is to measure the energy by conventional methods, the lateral faces and the input face of the scintillator plate P1 not being coupled to a photodetector array are coated with a white reflector with an air gap with the plate P1, so that they are reflective and scattering. This type of set-up is recommended particularly for measuring the energy of photons <250 KeV.

It is to be noted that there are two possible methods for measuring the energy of an incident photon. The temporal method which relates solely to unscattered photons, or 10 to 20% of emitted photons. This method operates especially if the energy of the incident photon is >250 keV. This method requires the non-coupled faces to be scattering and absorbent, for example painted black with a paint of index as high as possible to avoid reflection by step-index.

The classic method supposes that all emitted photons are captured. It is to be preferred if the energy of the photons to be detected is <250 KeV. This method requires that non-coupled faces are scattering and reflective, for example coated with a white reflector with an air gap with the crystal.

In particular, the detection system further comprises a module for estimating a valid Compton event in the plate P1, said module being capable of performing this estimation by identifying at least one first and one second extremum in the distribution of light inside said plate P1, said second extremum appears when the difference between the arrival time Ta of photons at A, and the arrival time Tb of photons at B is less than three times a transfer time Tt of the light in the plate P1, where Tt=nH/c with H the height of the plate.

To be validated as Compton scattering, the difference between the arrival time Ta−Tb must be less than three times the transfer time of the light in the crystal.

According to an embodiment of the invention, the detection system is characterized in that it further comprises a second scintillator plate P2, in that the plate P1 is finer than the second plate P2, in that the thickness of the scintillator plate P1 is such that the gamma photon undergoes Compton deviation at a point A of said plate P1; the second scintillator plate P2 has a thickness for absorbing at least 50% of the energy of the gamma radiation, said second plate being separated from the plate P1 by a distance 'D' of at least 10 mm, preferably greater than the thickness of the thickest plate. The system further includes a module for estimating a valid event, said module being capable of measuring on said second plate P2 a coincidence trigger in a time window less than the maximum transfer time of light between the plates P1 and P2 for identifying the valid Compton events. This coincidence time will be <1 ns in all cases.

Preferably, measuring of the energy is done conventionally by collecting via diffuse reflection a maximum of photons emitted on at least one of the two plates.

Preferably, the photodetector or fragmented photodetector array is of analog SI-PM type associated with an analog ASIC or of digital SI-PM type and the scintillator plates P1 and P2 are of lutetium silicate and/or lanthanum halide type.

The invention further relates to a process for determining spatiotemporal coordinates (X, Y, Z, T) and the energy E in at least two successive positions of a gamma photon having undergone Compton scattering performed in the system above. The process comprises the following steps:

- detection of the arrival time Ta of the unscattered photons emitted by the Compton scattering at a first point A;
- detection of the arrival time Tb of the unscattered photons emitted at a second point B by the total absorption of the gamma photon;
- determination of a circle $C_A$ corresponding to the unscattered photons emitted by the Compton deviation of the gamma radiation at point A, the diameter of the circle $C_A$ measures Xa, Ya and Za;
- determination of a circle $C_B$ corresponding to the unscattered photons emitted by the total absorption of the gamma photon at point B, the diameter of the circle $C_B$ measures Xb, Yb and Zb;

When the photons emitted during the Compton scattering at A and the total absorption at B remain in the same light cone of the unscattered photons emitted at A, the angle $\alpha_C < \theta_C$ where $\alpha_C$ is the Compton deviation and $\theta_C$ is the critical angle of total reflection and the circle $C_B$ is included in the circle $C_A$, in this first case, the process further comprises following steps:

- calculation of the diameters of said circles $C_A$ and $C_B$ to measure (Xa, Ya, Za) and (Xb, Yb, Zb);
- enumeration of the numbers of photons in said registered circles $C_A$ and $C_B$;
- definition of the energy of a gamma photon, said energies Ea and Eb being proportional to the number of photons counted inside said circles $C_A$ and $C_B$; or When the photon having undergone Compton deviation exits from the light cone, $\alpha_C > \theta_C$, the distance between the points A and B is large and the circles $C_A$ and $C_B$ are separate, in this second configuration, the process further comprises the following steps:

- determination of a first event A which is the first observed
- measuring of coordinates (Xa, Ya, Za, Ta) of said event at A and its energy Ea;
- determination of a second event B;
- measuring of coordinates of the event (Xb, Yb, Zb, Tb) and its energy Eb;
- calculation of the initial energy of the gamma photon which is equivalent to the sum of the energies Ea+Eb;
- determination of the Compton angle of deviation by reconstituting the position of the two interactions;
- deduction of the arrival direction of the gamma photon at point A, from the position of the point A (Xa, Ya, Za), the position of the point B (Xb, Yb, Zb) and the energies Ea and Eb; or When the photon having undergone Compton deviation exits from the light cone $\alpha_C > \theta_C$, the distance between the points A and B is small and the circles $C_A$ and $C_B$ are joined, in this third case, the process can further comprise the following steps:

adjustment of the distribution of light by an ellipsis of center A, the point B occupies one of the focuses, the semi minor axis corresponds to the radius RA of the circle $C_A$ and the semi major axis corresponds to the distance A–B+RB, where RB is the radius of the circle $C_B$;

determination of the position of the point A (Xa, Ya) given by the center of the ellipsis;

determination of the depth of interaction Za at A which is given by the semi major axis of the ellipsis (RA);

calculation of the time Ta by correcting the times measured with Za;

determination of the position of the point B (Xb, Yb) which is given by the focus of the ellipsis;

determination of the depth of interaction Zb at B which is given by RB calculated with the semi major axis of the ellipsis: by Distance (A–B)+RB;

calculation of the time Tb by correcting the times measured with Zb;

measuring of the total energy Ea+Eb by integrating the photons over the whole of said ellipsis;

measuring of the barycenter of the distribution of the photons in the ellipsis;

determination of the initial point of interaction A or B, said initial point is that which is the closest to the barycenter;

determination of the Compton angle of deviation $\alpha_C$ by reconstituting the position of the two interactions at A and at B.

In another way, when the circles $C_A$ and $C_B$ are joined and $\alpha_C > \theta_C$ the process can further comprises following steps:

adjustment of the overall distribution of light by a composition of two circles $C_A$ and $C_B$;

determination of the positions (Xa, Ya) and (Xb, Yb) of the respective interactions at A and at B, said positions are given by the center of each circle $C_A$ and $C_B$;

determination of the depth of the interactions Za and Zb, by determining the diameter of the circles $C_A$ and $C_B$;

measuring of the total energy Ea+Eb by integrating the photons over the whole of said composition;

determination of the barycenter of the overall distribution of light of photons in the composition of two circles;

determination of the initial point of interaction A or B, said initial point is that which is the closest to the barycenter of the overall distribution of light;

determination of the Compton angle of deviation $\alpha_C$ by reconstituting the position of the two interactions at A and at B.

The invention further comprises use of the detection system in the field especially of the astronomy of the nuclear industry and of the medical and of the industry to detect radioactive contamination.

BRIEF DESCRIPTION OF THE FIGURES

Other characteristics, details and advantages of the invention will emerge from the following description in reference to the appended figures in which.

DETAILED DESCRIPTION

The present invention uses a time camera capable of measuring at the same time the position in space, in time and the energy of each gamma photon. The principle of a time camera is taught in patent applications No. 1260596 FR and No. 1454417 FR by the same applicant.

In this type of time camera, for each scintillation event (photo-electric effect or Compton scattering) a circle corresponding to the unscattered photons which are the first detected is identified.

The unscattered photons are distributed in a cone whereof the apex is the place of interaction (X,Y,Z,T) and whereof the angle of opening is the total reflection angle on the output face.

When the gamma photon undergoes a photoelectric effect, there is one circle only. Hereinbelow the aim is to characterize the position and diameter of a circle and not the barycenter of distribution of light.

If the gamma photon undergoes Compton scattering then a photoelectric effect, there are two circles which appear almost coincident on the plane of the detectors. A good criterion experimentally for validating the presence or not of Compton scattering is that the difference between the times of arrival Ta–Tb of the two maximums of light must be under three times the transfer time of the light in the crystal.

Figure 1:
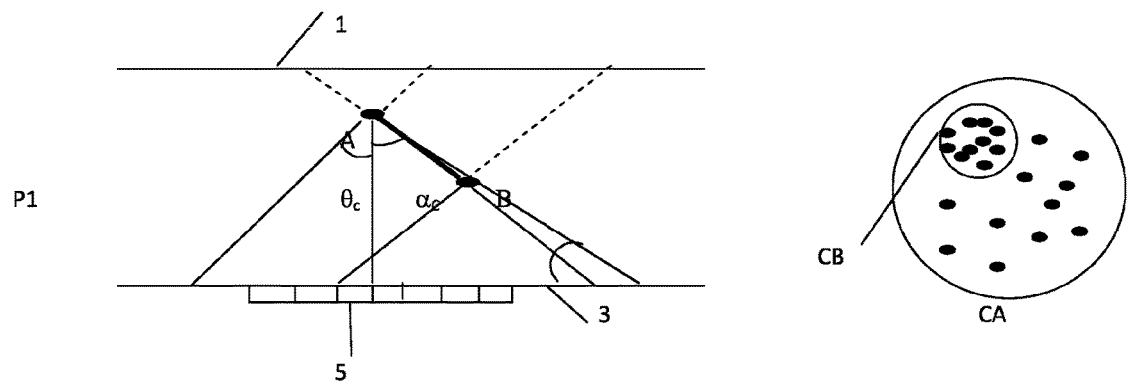
FIG. 1 shows the detection system according to the invention in the case of a plate P1 and when the photon having undergone Compton scattering of angle $\alpha_c$ remains in the same light cone ($\alpha_c$ less than $\theta_c$)
Figure 2:
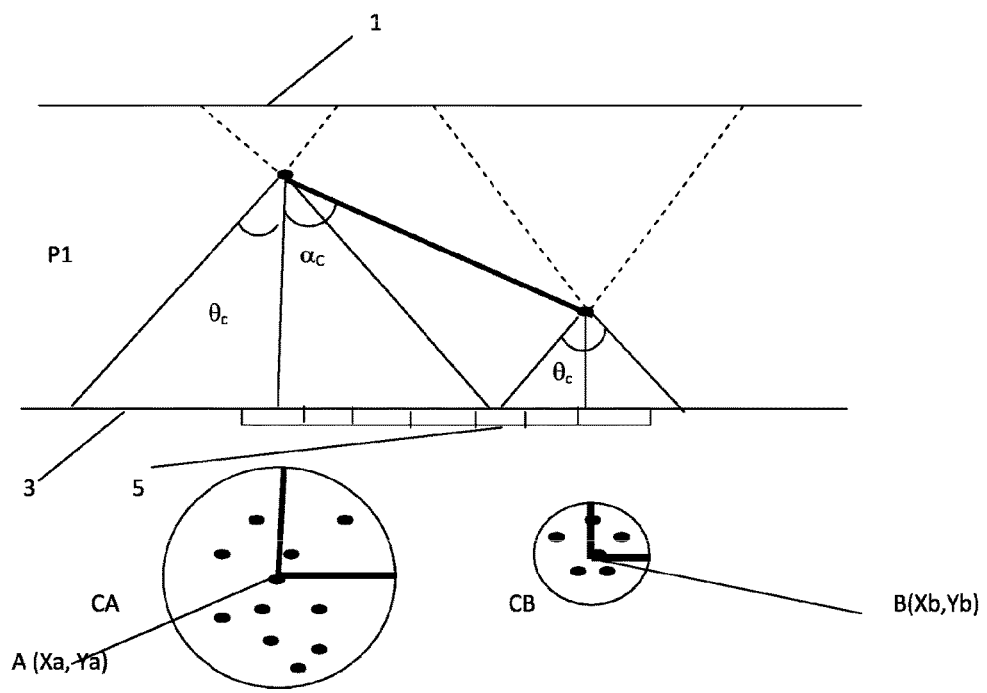
FIG. 2 shows the detection system according to the invention in the case of a plate P1 when the photon having undergone a Compton scattering of angle $\alpha_c$ exits from the light cone (deviation $\alpha_c$ greater than $\theta_c$), existence of two separate circles.

In the case where the gamma photon undergoes Compton deviation at point A (Xa, Ya, Za, Ta, Ea) before being absorbed at point B (Xb, Yb, Zb, Tb, Eb), the following three cases will be considered:

FIG. 1 shows the detection system according to the invention in a first case where the photon undergoes a Compton scattering of angle $\alpha_c$ remaining in the same light cone as the unscattered photons. The system comprises a plate P1, fitted with a photodetector array 5 associated with micro-electronic components 6. The plate P1 has a thickness greater than or equal to 10 mm. On this plate P1 the arrival time Ta of unscattered photons emitted by Compton scattering is detected at a first point A; then the arrival time Tb of photons having undergone a total absorption at a second point B is detected; and a circle $C_A$ corresponding to the photons emitted during Compton deviation and a circle $C_B$ corresponding to the photons emitted during complete absorption of the gamma photon are determined. In this first case, the Compton deviation of angle $\alpha_c$ is less than the angle $\theta_C$ where $\theta_C$ is the critical angle of total reflection. In this case which is the commonest, the unscattered photons emitted by the interaction all remain in the same light cone, but their distribution can have asymmetry i.e. the circle $C_B$ (corresponding to point B) included in the circle $C_A$ corresponding to point A. However, in the same manner as a photoelectric event, the diameter of the circle $C_A$ measures Xa, Ya and Za. Thus, the diameter of the circle $C_B$ measures Xb, Yb and Zb. Reconstitution of the interaction measures Ta and Tb. Enumeration of the number of photons in the circles $C_A$ and $C_B$ estimates the relative energy deposited at points A and B. In a simplified version of the processing only the biggest circle is considered (circle $C_A$). It is evident that the Compton effect $n_e$ does not modify the precision of the measuring of spatiotemporal coordinates of the point A. As shown in FIG. 2, the case where the photon having undergone a Compton scattering of angle $\alpha_c$ exits from the light cone is also considered. In this case the deviation $\alpha_c$ is greater than $\theta_c$. This gives separate events, i.e., the existence of two circles quasi-simultaneous in time, as compared to the case of the pile-up. Here too, there are two cases: either the two circles are joined (Distance A–B<Ra+Rb), or the two circles are separate (Distance A–B>Ra+Rb). FIG. 2 shows the case where the two circles $C_A$ and $C_B$ are separate. It is evident that this is Compton scattering if Tb–Ta is adjacent to Distance (A–B)/C. In this case each event is processed independently. The first event detected and/or according to the geometry the one corresponding to the most energy deposited is the initial event. The energy of the initial photon is equal to EA+EB. The position of the two points measures $\alpha_c$.

Figure 3:
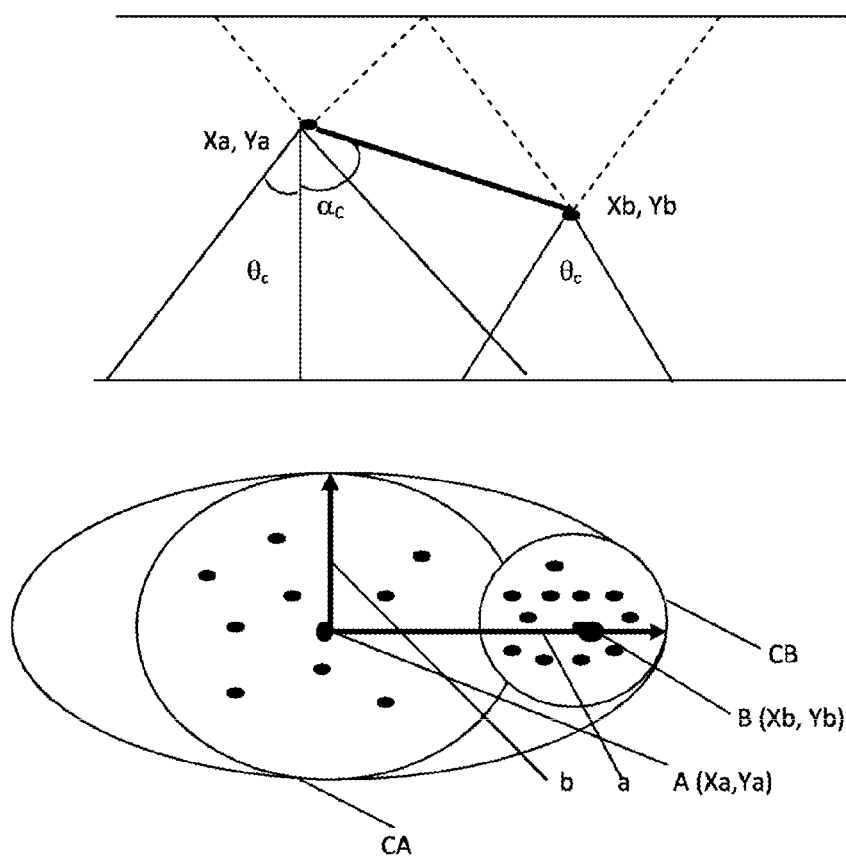
FIG. 3 shows the detection system according to the invention in the event where (deviation $\alpha_c$ greater than $\theta_c$), existence of two joined circles, the distribution of light being adjusted by an ellipsis.

In the case where the circles $C_A$ and $C_B$ are joined, it is evident that this is Compton scattering if Tb–Ta is adjacent to A–B/C. In this case, as shown in FIG. 3, the distribution of light can be adjusted by an ellipsis whereof the semi minor axis (b) corresponds to the radius of the first circle RA and semi major axis (a) corresponds to Distance A–B+RB. In this configuration, the essential precision in the estimation of coordinates Xa, Ya and Za is retained, despite the Compton scattering. The position of the point A (Xa, Ya) is given by the center of the ellipsis. The depth of interaction at A is given by the semi minor axis of the ellipsis, which calculates Za. Ta can then be calculated by correcting the times measured with Za. So, the position of the point B is given by the focus of the ellipsis (Xb, Yb). The depth of interaction at B is given by the semi major axis of the ellipsis (A–B+RB). Given A–B, RB is found, which calculates Zb. Tb can then be calculated by correcting the times measured with Zb. The energy E is measured by integrating the photons over the whole of said ellipsis. The total energy EA+EB is obtained. Calculating the barycenter of the distribution of the photons in the ellipsis can find the initial point of interactions A or B which is the closer to the barycenter.

Figure 4:
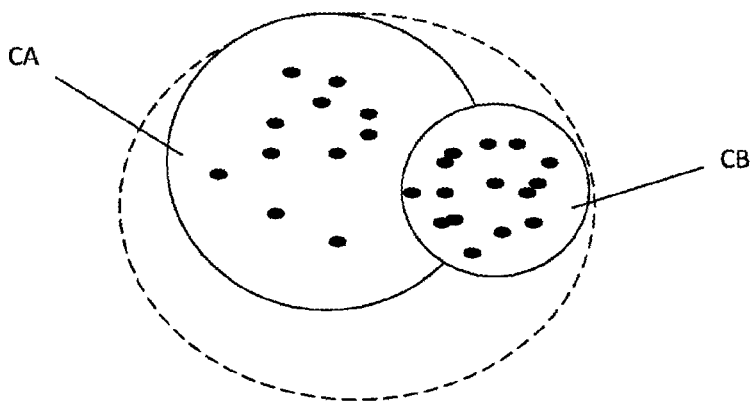
FIG. 4 shows the principle of FIG. 3, existence of two joined circles, the distribution of light being adjusted by a composition of two circles.

Another method in the event where the two circles $C_A$ and $C_B$ are joined is to adjust the distribution of light by a composition of two circles such as shown in FIG. 4 in dotted lines. In this case the center of each circle gives the position of the respective interactions Xa, Ya at A and Xb, Yb at B. The diameters of the circles $C_A$ and $C_A$ give the depth of interaction Za and Zb. The energy is measured by integrating the photons over the whole of said composition. The initial point of interaction A or B is that which is the closer to the barycenter of the overall distribution of light. Also, the reconstitution of the position of the two interactions estimates the Compton angle of deviation $\alpha_c$. The ratio EB/EA must verify the laws of the Compton scattering.

Figure 5:
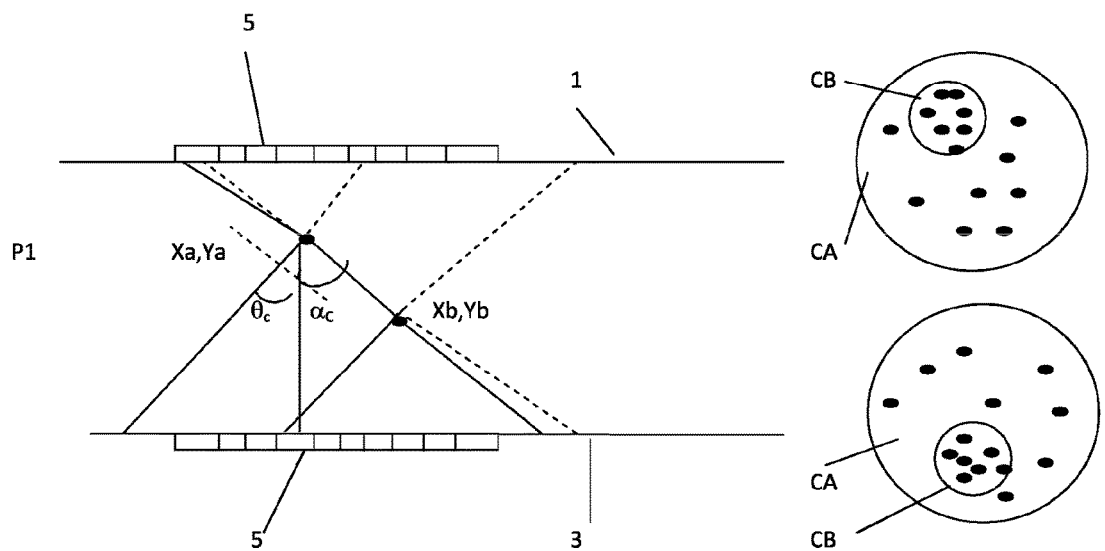
FIG. 5 shows the detection system according to the invention with the plate P1 fitted with two photodetector arrays respectively on an input face and an output face.

FIG. 5 shows the same case as FIG. 1, except that the input face 1 and the output face 3 of the plate P1 are covered in photodetectors segmented with a maximum filling density. In this case, the photons which have undergone Compton deviation of angle of deviation $\alpha_c$ are absorbed by the photodetector. The circle of the unscattered photons is seen on each side of the plate and exactly the same treatments described previously are carried out. But propagation of the gamma ray of the input face 1 towards the output face 3 introduces asymmetry between the two faces. In a certain way the image on the input face 1 is the inverse of the image on the output face 3.

The advantage of covering each side of the plate P1 of photodetectors 5 is obtaining two independent estimations of the coordinates of each event (X, Y, Z, T, E). Also, comparison of the distributions of light on each side of the plate dispels any ambiguities in reconstitution if the photon has undergone at least one Compton scattering. Also, the number of photons used for reconstruction is doubled and this improves the energy resolution for each photon since the energy resolution grows with the number of photons collected.

The drawback to the configuration hereinabove is in the cost of the micro-electronic components used on each plane of photodetectors. In fact, in this case the price of the electronics doubles. This configuration is interesting essentially on a thick plate and above all in the case of a single-plate Compton camera where the aim is to reconstitute the path of the gamma photon in the crystal. Also, this configuration fails to reject noise whether intrinsic to the scintillator or not. All events are analyzed whether emanating from the source or not.

For photons of known energy (PET) or known arrival direction (SPECT), the counting of events can be simplified. In this case in point, the sole aim is to determine the initial point of impact of the photon (XA, YA, ZA), its arrival time TA and the overall energy of the interaction EA+EB. In this case the double reading is advantageous.

It is evident that in all cases it is possible to correctly measure the position of initial interaction despite the Compton scattering. Also, it is possible to have an estimation of the vector AB between two successive interactions and the energy EA and EB deposited at each interaction. With such a system it is therefore possible to make a Compton camera with a single scintillator plate. A single-plate system will not be optimal in terms of performance, but it will be very advantageous in terms of cost and in terms of efficiency of detection (high percentage of gamma rays fully absorbed by the detector). If the Compton camera is used in a noisy environment such as LSO detector plates having strong intrinsic radiation and a high radiation rate, it is necessary to use a two-plate system. In fact, the time coincidence between detection on the two plates is an excellent way for countering noise. A valid Compton event must be detected almost simultaneously on both plates. The delay between 2 valid events may not be greater than plate transfer time P1 (c/n)+inter-plate transfer time (c)+plate transfer time P2 (c/n) or a time <1 ns.

In another embodiment of the system, to eliminate reflection of gamma rays on the faces not used for detection (lateral faces and input face if there is a single array of detectors only), the latter are treated such that absorption of incident photons is maximum there. In fact, if the photons are reflected onto these faces they sound detection of the circle of the unscattered. The fact of treating all faces not used for detection, faces called "sterile", increases the integration time of time images (i.e. having them go from 750 ps to 1500 ps) by 50 to 100% for a given rate of detected unscattered photons (i.e. 90% of photons detected are unscattered). This mode is possible only if the energy is measured by the temporal method, i.e., for energies >250 KeV in the LSO. The faces not coupled to an array of detectors are rough and treated so as to absorb as far as possible the incident radiation to prevent parasite reflections towards the detectors.

This treatment must avoid reflections on the faces called "sterile", especially by an step-index. The treatment can comprise an anti-reflective deposit of any known type, followed by deposit of a layer of absorbent material. It can further be constituted by a deposition of a high-index resin (n>1.5) charged with absorbent material.

If the "sterile" faces are simply painted black conventionally due to the considerable contrast of index between the crystal (n=1.9) and the paint (n<1.5) most of the photons are reflected towards the interior of the crystal.

The faces coupled to detector arrays are preferably polished. Coupling between these faces and the detectors is achieved by a low-index medium (n<1.5) to create a total reflection angle.

For producing a time camera covering a wide energy spectrum (100 KeV-2 MeV) it can be advantageous for at least one of the two plates to measure the energy of photons by the conventional method (white scattering processing).

Simulation of Three Cases of Compton Effect

Simulation conditions are the following:
LaBr3:Ce crystal of thickness 30 mm of index n=1.9 coupling with the photodetector with lubricant (n=1.4). For each image, the position of the photons detected at a given time is indicated:

200 ps
700 ps
16000 ps (16 ns)

Each image also shows a simulation of what is seen on each segmented photodetector.

Point A of the Compton scattering positioned at Z=5 mm for the three cases:

Case No. 1 (alpha<theta) total absorption point B at Z=15 mm.
Case No. 2 (alpha>theta) adjacent Compton: total absorption point B at Z=15 mm.
Case No. 3 (alpha=pi/2) disjoined Compton: total absorption point at Z=5 mm.

In current photodetectors, detection of photons is subject to threshold effects. If the aim is to dispense with background noise from the detectors (dark counts) it is necessary to detect 1.5 to 2 photoelectrons. Since the integration time Ti is brief, typically under 2 ns, the number of photons to be detected during Ti can be less than the threshold for the peripheral pixels. The integration time is given by the time on completion of which the number of photons detected outside the circle of the unscattered photons passes a certain threshold. The number of photons emitted by interaction in the angular sector of the unscattered photons is constant. The density of photons/pixels depends on the diameter of the circle. The maximum diameter of the circle depends on the thickness of the crystal. On can therefore play on the density of photons/pixels by playing on the thickness of the crystal scintillator. So, the more finely segmented the detector, the more advantageous it could be to use thin crystals.

Also, since the integration time Ti (less than 2 ns) is brief relative to the possibilities of better current electronics, it is advantageous to search for means for counting photons longer. The integration time given by the time on completion of which the number of photons detected outside the disc of the unscattered photons passes a certain threshold (for example 90%), the passing of this threshold depends essentially on the number of photons scattered on the input face 1 of the crystal, or on the lateral faces for the pixels located at less than a thickness of crystal of the edges. Given that for a Compton imager only the unscattered photons can be used for measuring X, Y, Z, T, E, it can be advantageous to eliminate all the other photons.

A known way of achieving this can be to paint the lateral faces and the input face 1 (the faces not used for detection) black to absorb all the photons which exit the crystal. But given that the index of the paint (typically 1.5) is less than the index of the crystal 1.8 to 1.9, most of the photons are reflected by the step-index and will disrupt the signal. A more advantageous way of executing the invention is therefore either to find a black product of index close to that of the scintillator, or to perform anti-reflection treatment by any known means on the lateral faces and the input face 1 of the crystal, then apply a black absorbent deposit to this anti-reflection treatment.

Another way of creating this result can be to deposit on these faces of the crystal a high-index "n" resin (n>1.5) preferably n greater than 1.7 charged with absorbent particles.

This treatment has the following advantages: considerably decreasing the number of photons detected outside the light cone of the unscattered photons increases the time during which the first photons can be counted for defining the position of the circle.

This system also substantially limits edge effects and therefore exploits the entire detector for imaging.

This anti-reflection treatment can be performed by layers of interferences, photonic crystals or progressive adaptation of index obtained by nanostructuring such as disclosed in European patent application No. 14305365.0 filed on Mar. 13, 2014 "Structuration for optimizing the collection of photons in the scintillator crystals and associated technological solutions".

Figure 6:
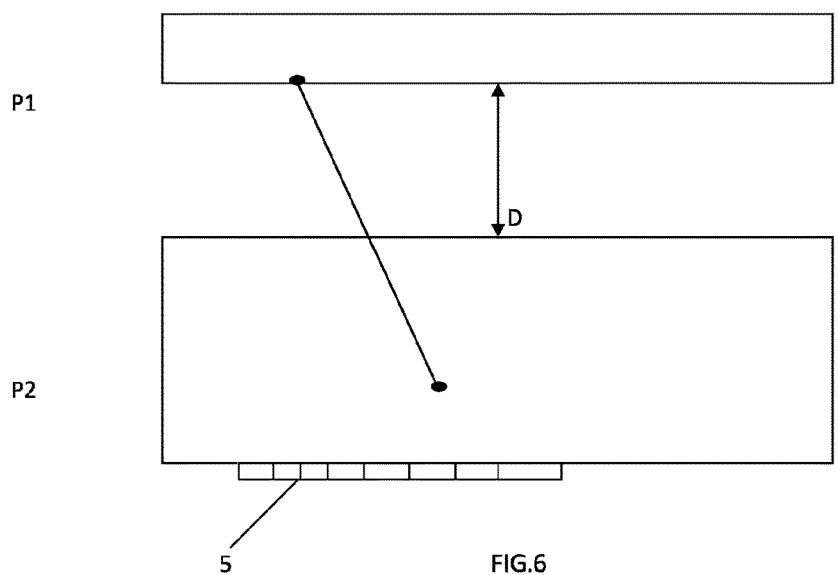
FIG. 6 shows an embodiment of the system with two scintillator plates P1 and P2.

FIG. 6 shows a second embodiment of the system according to the invention comprising two scintillator plates P1 and P2, arrays of photodetector 5 and the associated electronics, not shown, the arrays being stuck to each plate P1 and P2. The plate P1 is finer than the plate P2. On this plate P1 the aim is to obtain Compton scattering at a first point A of coordinates (Xa, Ya, Za, Ta, Ea). The second plate P2 is thicker than the plate P1. The thickness of said second plate P2 absorbs at least 50% of the energy of the gamma ray at a point B of coordinates (Xb, Yb, Zb, Tb, Eb). The second plate P2 is separated from the plate P1 by a distance 'D' of at least 10 mm, preferably 30 mm. The system comprises a module for estimating a valid Compton event. Said module is capable of measuring on the second plate P2 a coincidence trigger Tb in a time window less than 1 ns for identifying the valid Compton events.

Let D' be the distance between the 2 plates of the Compton camera, EP1 the thickness of the first plate, EP2 the thickness of the second plate. The maximum transfer time of a photon perpendicular to the detector is:

The time Tmax=EP1*(n/c)+D'/c+EP2*(n/c). To simplify, in the case of oblique propagation, T<1.5 Tmax is considered.

The detection times of a Compton event detected on the two plates is to therefore verify: D'/c<TB−TA<1.5 Tmax. In the case of an LaBr3 system optimized for 511 KeV (EP1=10 mm, D'=30 mm, EP2=30 mm). This would give: 100 ps<TB−TA<380 ps.

This very strict temporal condition rejects all those events which are not strict Compton scatterings. Such precise time windowing is possible with the electronics developed for temporal cameras and for detectors of digital Si-PM type.

The probability of two coincident events in such a short time (outside Compton) is very low. This windowing therefore enables considerable reduction in the noise of the detectors.

It is therefore evident that the invention enables two types of Compton camera to be made: 1) A single-plate camera having moderated but compact precision and sensitivity and of moderate cost. 2) A highly sensitive multi-plate camera due to rejection of noise by the time windowing, more precise due to better angular definition of the path of the gamma photon, but bulkier and more expensive.

It is clear that in the detection system according to the invention constituted by a single plate P1 or two plates P1 and P2 a good location of each event is maintained in a detector in the event where the photon has undergone a Compton effect and the energy of an event in a detector of time camera type is also measured precisely in the event where the photon has undergone a Compton effect.

Also, an improved Compton camera can be made by combining one or more detectors of time camera type.

Another interest of the system according to the invention is its use in the fields especially of medicine and astronomy. The detection system according to the invention can also be used in the industry for detecting radioactive contamination.

Many combinations can be possible without departing from the scope of the invention; those skilled in the art will select one or the other as a function of economic, ergonomic, dimensional or other restrictions to be respected.

The invention claimed is:

1. A detection system for detecting gamma radiation, of Compton camera type, comprising:
    a source of gamma radiation,
    at least one scintillator plate of a scintillator crystal, emitting photons when exposed to said source of gamma radiation, with a rise time to light peak shorter than 1 ns and having a thickness greater than or equal to 5 mm,
    an array of segmented photodetectors for detection of said photons, and
    a dedicated rapid reading microelectronics, for reading the signal emitted by said segmented photodetectors at said detections,
wherein the system is configured for measuring the times of said detections with a time resolution smaller than said rise time to light peak, and thereby perform a discrimination, among the detected photons, between the unscattered photons and the scattered photons, based on their times of detections,
wherein the system is further configured for:
    measuring the spatiotemporal coordinates (X, Y, Z, T) and the energy E in at least two successive positions of a gamma photon when said photon undergoes Compton deviation at a first point A before being absorbed at a second point B, by recognizing circles of unscattered photons corresponding to each scintillation interaction, A and B, according to said discrimination,
    an identification of Compton deviation events, by selecting the couples of detections having a delay between said scintillation interactions A and B which is lower than a predetermined threshold, so as to allow a reconstitution of a Compton path within said at least one scintillator plate.

2. The detection system according to claim 1, wherein said at least one scintillator plate is a single scintillator plate having a thickness greater than or equal to an average free path, within said scintillator crystal, of gamma rays emitted by said source and wherein said identification of Compton deviation events is performed for such events within said single scintillator plate.

3. The detection system according to claim 2, further comprising two photodetector arrays each disposed on an input face and an output face of said scintillator plate, respectively, to improve precision of said reconstitution of the Compton path within the scintillator plate.

4. The detection system according to claim 3, wherein the input face and the output face of the scintillator plate are polished and coupled to the photodetector array by a media of index n less than 1.5 to arrange a total reflection angle.

5. The detection system according to claim 1, wherein the lateral faces and an input face of said scintillator plate which are not coupled to a photodetector array are rough or treated such that the absorption of incident photons or the diffuse reflection of photons are limited.

6. The detection system according to claim 1 wherein the input face of said scintillator plate which is not coupled to a photodetector array is painted black to limit the reflection on said input face.

7. The detection system according to claim 1, wherein the lateral faces and an input face of said scintillator plate, which are not coupled to a photodetector array, are coated with a white reflector with an air gap between this reflector and said scintillator plate.

8. The detection system according to claim 2 wherein said identification of Compton deviation events, by selecting interactions A and B separated by a delay lower than the predetermined threshold, is performed by module of the system identifying at least one first and one second extremum in the distribution of light inside said plate, said second extremum appearing while the difference between the arrival time Ta of photons at A, and the arrival time Tb of photons at B is less than said threshold which corresponds to three times a transfer time Tt of the light in the plate, where Tt=nH/c with H the height of the plate.

9. The detection system according to claim 1, wherein:
    the system further comprises a second scintillator plate, which has a thickness thinner than the thickness of the first scintillator plate and which is disposed between said source of gamma radiation and the first scintillator plate, such that the gamma rays emitted by said source may undergo Compton deviation at a point A in said second scintillator plate, while said first scintillator plate has a thickness for absorbing at least 50% of the energy of the gamma radiation, said second scintillator plate being separated from said first scintillator plate by a distance 'D' of at least 10 mm, preferably greater than the thickness of the thickest plate,
    said identification of Compton deviation events, by selecting interactions A and B separated by a delay lower than the predetermined threshold, is performed by a module for estimating valid Compton deviation events, measuring a coincidence trigger between said second scintillator plate and said first scintillator plate in a time window smaller than said threshold which corresponds to the maximum transfer time of light between said second scintillator plate and said first scintillator plate.

10. The detection system according to claim 1, wherein the measuring of the energy is done conventionally by collecting via diffuse reflection a maximum of photons emitted on at least one of the two plates.

11. The detection system according to claim 1, wherein the fragmented photodetector array is of analog SI-PM type associated with an analog ASIC or of digital SI-PM type.

12. The detection system according to claim 1, wherein the scintillator plates and are of lutetium silicate and/or lanthanum halide type.

13. A process for determining spatiotemporal coordinates (X, Y, Z, T) and the energy E in at least two successive positions of a gamma photon having undergone Compton deviation performed in a system according to claim 1 comprising:

detection of an arrival time Ta of the unscattered photons emitted by the Compton deviation at a first point A;

detection of an arrival time Tb of the unscattered photons emitted at a second point B by the total absorption of the gamma photon;

determination of a circle $C_A$ corresponding to the unscattered photons emitted by the Compton deviation of the gamma radiation at point A, the diameter of the circle $C_A$ measuring Xa, Ya and Za;

determination of a circle $C_B$ corresponding to the unscattered photons emitted by the total absorption of the gamma photon at point B, the diameter of the circle $C_B$ measuring Xb, Yb and Zb;

wherein:

when the photons emitted during the Compton scattering at A and the total absorption at B remain in the same light cone of the unscattered photons emitted at A, the angle $\alpha C < \theta C$ where $\alpha C$ is the Compton deviation and $\theta C$ is the critical angle of total reflection and the circle $C_B$ is included in the circle $C_A$, the process further comprises:

calculation of the diameters of said circles $C_A$ and $C_B$ to measure (Xa, Ya, Za) and (Xb, Yb, Zb);

enumeration of the numbers of photons in said registered circles $C_A$ and $C_B$;

definition of the energy of a gamma photon, said energies Ea and Eb being proportional to the number of photons counted inside said circles $C_A$ and $C_B$;

or when the photon having undergone Compton deviation exits from the light cone, $\alpha C < \theta C$, the distance between the points A and B is large and the circles $C_A$ and $C_B$ are distinct from each other, the process further comprises:

determining a first event A corresponding to the strongest energy;

measuring coordinates (Xa, Ya, Za, Ta) of said event at A and its energy Ea;

determining a second event B corresponding to the lowest energy;

measuring coordinates of the event (Xb, Yb, Zb, Tb) and its energy Eb;

measuring the initial energy of the gamma photon equivalent to the sum of the energies Ea+Eb;

determining a Compton angle of deviation by reconstituting the position of the two interactions;

deducing the arrival direction of the gamma photon, from the position of the point A (Xa, Ya, Za), the position of the point B (Xb, Yb, Zb) and the energies Ea and Eb;

or when the photon having undergone Compton deviation exits from the light cone $\alpha C < \theta C$, the distance between the points A and B is small and the circles $C_A$ and $C_B$ are joined, the process can comprise the following steps:

adjusting the distribution of light by an ellipsis of center A, the point B occupies one of the focuses, the semi minor axis corresponds to the radius RA of the circle $C_A$ and the semi major axis corresponds to the distance A–B+RB, where RB is the radius of the circle $C_B$;

determining the coordinates Xa, Ya of the point A given by the center of the ellipsis;

determining the depth of interaction Za at A which is given by the semi major axis of the ellipsis RA;

calculating the time Ta by correcting the times measured with Za;

determining the coordinates Xb, Yb of the point B which is given by the focus of the ellipsis;

determining the depth of interaction Zb at B which is given by RB calculated from the semi major axis of the ellipsis: by Distance (A–B)+RB;

calculating the time Tb by correcting the times measured with Zb;

measuring the total energy Ea+Eb by integrating the photons over the whole of said ellipsis;

measuring the barycenter of the distribution of the photons in the ellipsis;

determining the initial point of interaction A or B, said initial point is that which is the closest to the barycenter;

determining the Compton angle of deviation $\alpha C$ by reconstituting the position of the two interactions at A and at B.

14. The process according to claim 13, wherein, when the circles $C_A$ and $C_B$ are joined and $\alpha C < \theta C$ wherein the process further comprises:

adjusting the overall distribution of light by a composition of two circles $C_A$ and $C_B$;

determining the coordinates Xa, Ya and Xb, Yb of the interactions at A and at B, respectively, said positions are given by the center of each circle $C_A$ and $C_B$;

determining the depth of the interactions Za and Zb, by determining the diameter of the circles $C_A$ and $C_B$;

measuring the total energy Ea+Eb by integrating the photons over the whole of said composition;

determining the barycenter of the overall distribution of light of photons in the composition of two circles;

determining the initial point of interaction A or B, said initial point is that which is the closest to the barycenter of the overall distribution of light;

determining the Compton angle of deviation $\alpha C$ by reconstituting the position of the two interactions at A and at B.

* * * * *